United States Patent [19]

Bezwada et al.

[11] Patent Number: 5,703,200
[45] Date of Patent: Dec. 30, 1997

[54] ABSORBABLE COPOLYMERS AND BLENDS OF 6,6-DIALKYL-1,4-DIOXEPAN-2-ONE AND ITS CYCLIC DIMER

[75] Inventors: Rao S. Bezwada, Whitehouse Station; Steven C. Arnold, Sparta; Constance Ace, Whitehouse, all of N.J.

[73] Assignee: Ethicon, Inc., Somerville, N.J.

[21] Appl. No.: 616,799

[22] Filed: Mar. 15, 1996

[51] Int. Cl.$^6$ .................................................. C08L 71/02
[52] U.S. Cl. ........................ 528/354; 528/370; 528/361; 525/63; 525/88; 525/415; 525/481; 424/426; 424/430; 424/444; 424/446; 424/448; 424/486
[58] Field of Search ........................... 525/63, 88, 415, 525/461; 528/354, 370, 361; 424/426, 430, 433, 444, 446, 448, 486

[56] References Cited

U.S. PATENT DOCUMENTS

| | | | |
|---|---|---|---|
| 3,063,967 | 11/1962 | Schultz | 260/78.3 |
| 3,063,968 | 11/1962 | Schultz | 260/78.3 |
| 3,351,485 | 11/1967 | Langner | 117/147 |
| 4,052,988 | 10/1977 | Doddi et al. | 128/335.5 |
| 4,190,720 | 2/1980 | Shalaby | 528/354 |
| 4,470,416 | 9/1984 | Kafrawy et al. | 528/354 |
| 5,252,701 | 10/1993 | Jarret et al. | 528/354 |
| 5,442,032 | 8/1995 | Arnold et al. | 528/354 |
| 5,464,929 | 11/1995 | Bezwada et al. | 528/361 |
| 5,595,751 | 1/1997 | Bezwada et al. | 424/422 |
| 5,607,687 | 3/1997 | Bezwada et al. | 424/426 |
| 5,618,552 | 4/1997 | Bezwada et al. | 424/426 |
| 5,620,698 | 4/1997 | Bezwada et al. | 424/426 |

FOREIGN PATENT DOCUMENTS 460 428 A2  6/1991  European Pat. Off. .

Primary Examiner—James J. Seidleck
Assistant Examiner—Duc Truong
Attorney, Agent, or Firm—Hal Brent Woodrow

[57] ABSTRACT

This invention provides various copolymers comprising a first repeating unit of the chemical formula:

$$\mathrm{+CH_2\underset{\underset{R_1}{|}}{\overset{\overset{R_2}{|}}{C}}CH_2OCH_2CO_2+}$$

in which $R_1$ and/or $R_2$ are alkyl groups and a second repeating units generally having the chemical formula:

$$+CHRCO_2+$$
$$+[CH_2]_5CO_2+$$
$$+CH_2CH_2OCH_2CO_2+$$
$$+CH_2CH_2CH_2OCO_2+$$
$$+CH_2CH_2CH_2OCH_2CO_2+$$
$$+CH_2CH_2OCH_2CH_2CO_2+$$

and combinations of two or more thereof wherein R is a hydrogen atom or a methyl group and the first repeating unit is less than 45 weight percent of the total weight of the copolymer. This invention also relates to use of these copolymers in the fabrication of absorbable surgical devices such as sutures and as coatings for medical devices. Additionally, described are blends and polyoxaesters containing the first repeating unit.

62 Claims, No Drawings

ABSORBABLE COPOLYMERS AND BLENDS OF 6,6-DIALKYL-1,4-DIOXEPAN-2-ONE AND ITS CYCLIC DIMER

FIELD OF THE INVENTION

This invention relates to copolymers and blends derived from 6,6-dialkyl-1,4-dioxepan-2-one and its cyclic dimer, 3,3,10,10-tetra-alkyl-1,5,8,12-tetraoxacyclotetradecane-7,14-dione, and especially to crystalline copolymers and blends thereof having mechanical and biological properties which are desirable for the preparation of absorbable surgical sutures and devices.

BACKGROUND OF THE INVENTION

In U.S. Pat. No. 5,442,032, Arnold et al describe the synthesis and characterization of poly[1,4-dioxepan-2-one] and a variety of statistically random and block copolymers composed of the repeating units of glycolide, L-lactide, 1,4-dioxan-2-one, and 1,4-dioxepan-2-one. Because poly[1,4-dioxpan-2-one] was slow to crystallize, only copolymers with reasonably fast crystallization rates were successfully spun into fibers. In other words, only copolymers composed predominately of repeating units of glycolide, L-lactide, or 1,4-dioxan-2-one were found to be melt processable.

In contrast, homopolymers and copolymers of 1,4-dioxepan-2-one were described by Doddi et al. in U.S. Pat. No. 4,052,988 for use as absorbable synthetic sutures, tendons and the like. The copolymers disclosed by Doddi et al. were described as containing predominately 1,4-dioxepan-2-one and up to 50 weight percent of another copolymerizable monomer such as lactide or glycolide.

Similarly, U.S. Pat. No. 5,252,701, Jarrett et al., also describes copolymers of 1,4-dioxepan-2-one and other fast reacting monomers such as glycolide and lactide. This patent describes a block copolymer formed by a two stage polymerization process. In the first stage of this process, a prepolymer is formed containing predominately a monomer such as 1,4-dioxepan-2-one, the remainder of the prepolymer being a monomer such as glycolide or lactide. In the second stage of the polymerization, the prepolymer is reacted with an additional lactone monomer to provide a segmented block copolymer. Unfortunately, neither Doddi or Jarrett et al. describes the physical properties of polymers containing 1,4-dioxepan-2-one.

The structural isomer of 1,4-dioxepan-2-one, namely 1,5-dioxepan-2-one, has also been studied. U.S. Pat. Nos. 4,190,720 and 4,470,416 describe copolymers of 1,5-dioxepan-2-one and ε-caprolactone, glycolide, or lactide. In addition, the homopolymerization of 1,5-dioxepan-2-one and its cyclic dimer has been investigated. Albersson et al. (Macromolecules 1989, 22, 3838–3846; Makromol. Chem. Macromol. Symp. 1992, 53, 221–231; Macromolecules 1994, 27, 5556–5562; J. Biomater. Sci. Polymer Edn. 1994, 6 (5) 411–423; JMS-Pure Appl. Chem. 1995, A32 (1) 41–59; Polymer 1995, 36 (19) 3753–3759) have polymerized 1,5-dioxepan-2-one and its cyclic dimer. The resulting poly[1,5-dioxepan-2-one] was completely amorphous with a glass transition temperature of −39° C. Since poly[1,5-dioxepan-2-one] is an amorphous elastomer, it can only be used as an absorbable toughening agent either as a discreet phase in a polymer blend or composite, or as a segment in a block copolymer.

Surprisingly, we have discovered that poly[6,6-dimethyl-1,4-dioxepan-2-one] is a crystalline polymer with a substantially faster crystallization rate and higher melting point range than poly[1,4-dioxepan-2-one].

SUMMARY OF THE INVENTION

We have discovered a new class of synthetic polymeric materials that are bioabsorbable and may be used to produce surgical devices such as sutures, sutures with attached needles, molded devices, drug delivery matrices, coatings, lubricants and the like. The invention also contemplates a process for producing the bioabsorbable polymers and copolymers. The aliphatic polyesters of the present invention are copolymers comprising a first repeating unit made from 6,6-dialkyl-1,4-dioxepan-2-one having the chemical formula:

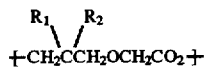

in which $R_1$ and/or $R_2$ are independently alkyl groups selected from the group consisting of methyl, ethyl and propyl groups and a second repeating unit is generated from a monomer selected from the group of glycolide, lactide (l, d, dl and meso), 3-methyl-1,4-dioxan-2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1,3-dioxan-2-one, epsilon-caprolactone and combinations thereof and the first repeating unit is less than 45 weight percent of the total weight of the copolymer. Preferred are second repeating units having a chemical formula selected from the group consisting of:

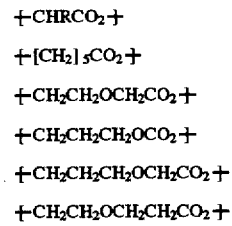

and combinations of two or more thereof wherein R is selected from the group consisting of a hydrogen atom, methyl group, ethyl group and propyl group. The copolymers of this invention can be readily melt spun using conventional techniques. The fibers prepared from these copolymers have the combination of mechanical and biological properties necessary for use as an absorbable monofilament surgical suture. By varying the molar ratio of first and second repeating units in a statistically random copolymer, or by varying the composition or concentration of prepolymer in a segmented block copolymer, the compliance, the in vivo breaking strength retention, and the absorption profile can be modified significantly. In this way, the biophysical properties of the copolymers of this invention can be tailored for specific applications. These copolymers will generally have a number average molecular weight of less than 100,000 g/mole.

The copolymers of this invention may also be fashioned into surgical devices by conventional melt processing techniques. For instance, these copolymers may be fabricated into orthopedic pins, screws, clamps, and plates; surgical knits or woven fabrics (such as medical dressings, hernia patches, gauze, meshes, fabrics, sheets, felts or sponges); surgical staples, hemostatic clips; suture knot clips; hooks; buttons; snaps; bone substitutes (such as vertebral discs and mandible prostheses); vascular implants and the like.

Additionally, the inventive copolymers may also be used as coatings for sutures and the like to improve the knot strengths and the tiedown properties and to reduce the tissue drag of sutures.

In further embodiments of the present invention there are also provided blends and polyoxaesters containing polymers or polymer segments made from 6,6-dialkyl-1,4-dioxepan-2-one.

DETAILED DESCRIPTION OF THE INVENTION

We have discovered a new class of synthetic polymeric materials that are bioabsorbable and may be used to produce surgical devices such as sutures, sutures with attached needles, molded devices, drug delivery matrices, coatings, lubricants and the like. The invention also contemplates a process for producing the bioabsorbable polymers and copolymers. The aliphatic polyesters of the present invention are copolymers comprising a first repeating unit of chemical formula:

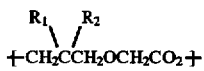

in which $R_1$ and/or $R_2$ are independently alkyl groups selected from the group consisting of methyl, ethyl and propyl groups. Preferably $R_1$ and $R_2$ will be the same alkyl groups. It is currently preferred for $R_1$ and $R_2$ to be methyl groups. The second repeating unit may be generated from a monomer selected from the group consisting of glycolide, lactide (1, d, dl and meso), 3-methyl-1,4-dioxan-2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1,3-dioxan-2-one, epsilon-caprolactone, and combinations thereof. Currently it is preferred for the second repeating unit to have a chemical formula selected from the group consisting of:

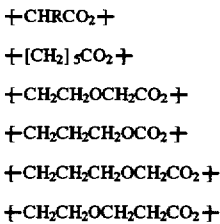

and combinations of two or more thereof wherein R is a hydrogen atom, methyl group, ethyl group, propyl group and combinations thereof.

The weight percent of repeating units derived from 6,6-dialkyl-1,4-dioxepan-2-one will be in the range of from about 1 weight percent to about 45 weight percent, and most preferably, in the range of from about 5 weight percent to about 30 weight percent.

The polymers of the present invention may be statistically random copolymers, block copolymers, or segmented block copolymers. Statistically random copolymers are prepared by copolymerizing 6,6-dialkyl-1,4-dioxepan-.2-one or its cyclic dimer with one or more lactone monomers. The use of the cyclic dimer of 6,6-dialkyl-1,4-dioxepan-2-one would produce a statistically random copolymer with an initial sequence distribution different from the copolymer formed using the 6,6-dialkyl-1,4-dioxepan-2-one. However, since transesterification reactions occur among the copolymer chains, it may be possible to find reaction conditions using the cyclic dimer of 6,6-dialkyl-1,4-dioxepan-2-one which would form a copolymer of the same sequence distribution that would be produced using 6,6-dialkyl-1,4-dioxepan-2-one. The choice to use 6,6-dialkyl-1,4-dioxepan-2-one or its cyclic dimer would depend on the desired copolymer microstructure and its physical properties; in some cases, 6,6-dialkyl-1,4-dioxepan-2-one may be the most appropriate monomer to employ; in other cases, its cyclic dimer may be. Preferably, statistically random copolymers of 6,6-dialkyl-1,4-dioxepan-2-one and one or more lactone monomers will contain from about 1 weight percent to about 45 weight percent of the repeating units of 6,6-dialkyl-1,4-dioxepan-2-one, and most preferably, from about 5 weight percent to about 30 weight percent of the repeating units of 6,6-dialkyl-1,4-dioxepan-2-one.

Segmented block copolymers are prepared in a two stage polymerization. In the first stage, a prepolymer is formed. In the second stage, the prepolymer is usually copolymerized with a monomer composition different from the prepolymer. For example, a prepolymer could be formed from a homopolymer of 6,6-dialkyl-1,4-dioxepan-2-one or its cyclic dimer and then reacted with one or more lactone monomers. The inherent viscosity of the prepolymer used in the segmented block copolymer may vary from about 0.5 to about 2.5 dL/g as measured in a 0.1 g/dL solution of hexafluoroisopropanol at 25° C. The prepolymer content of the segmented block copolymer can vary; however, as a general guideline, the weight percent of prepolymer will be in the range of from about 1 to about 99 weight percent. Because of transesterification reactions occurring among the polymer chains, these copolymers would have substantially the following chemical structure:

wherein A is a block composed primarily of repeating units of the chemical formula:

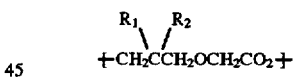

in which $R_1$ and/or $R_2$ are alkyl groups selected from the group consisting of methyl, ethyl, propyl and combinations thereof; and B is a block composed primarily of repeating units derived from monomers selected from the group consisting of glycolide, lactide (1, d, dl and meso), 3-methyl-1,4-dioxan-2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1,3-dioxan-2-one, epsilon-caprolactone, and combinations thereof. Preferably B will be composed primarily of repeat units having a chemical formula selected from the group consisting of:

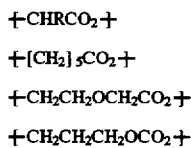

-continued $+CH_2CH_2CH_2OCH_2CO_2+$ $+CH_2CH_2OCH_2CH_2CO_2+$

The extent to which the repeating units are scrambled by transesterification reactions will depend on the reaction conditions used in both stages of the polymerization. Some of the reaction variables that would affect the amount of transesterification that occurs include the temperature, the reaction times, the catalyst and its concentration, and the molar ratio of monomer to initiator, i.e., the concentration of chain ends.

In another embodiment of the present invention, the prepolymer may be formed from one or more lactone monomers which may include 6,6-dialkyl-1,4-dioxepan-2-one or its cyclic dimer. The resulting prepolymer is then reacted with one or more other lactone monomers which may include 6,6-dialkyl-1,4-dioxepan-2-one or its cyclic dimer in a second polymerization. Suitable monomers for copolymerization are selected from the group consisting of glycolide, lactide (l, d, dl and meso), 3-methyl-1,4-dioxan-2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1,3-dioxan-2-one, epsilon-caprolactone and combinations thereof. Preferred are monomers for copolymerization are lactone monomers are selected from a group consisting of glycolide, L-lactide, D-lactide, D,L-lactide, meso-lactide, 1,4-dioxan-2-one, ε-caprolactone, 1,3-dioxan-2-one, 1,4-dioxepan-2-one, 1,5-dioxepan-2-one, and valerolactone. The only compositional requirement is that the copolymer contains 6,6-dialkyl-1,4-dioxepan-2-one and the weight percent of repeating units of 6,6-diaikyl-1,4-dioxepan-2-one in the segmented block copolymer be less than 45 weight percent overall. By varying the amounts of 6,6-dialkyl-1,4-dioxepan-2-one or its cyclic dimer, the solubility of the prepolymer in the second batch of molten monomers can be adjusted so that the prepolymer dissolves rapidly. In addition, the length of the blocks can be controlled to some extent by the reaction conditions which determine the amount of transesterification that occurs among the copolymer chains, by the weight ratio of the prepolymer to the sum of the monomers in the second stage of the polymerization, by the molecular weight of the prepolymer, and by the catalyst concentration. These factors can be varied to achieve the desired breaking strength retention and absorption profiles of a surgical device made from these copolymers. As a general guideline, the prepolymers may have an inherent viscosity in the range of from about 0.5 to about 2.5 dL/g as measured in a 0.1 g/dL solution of hexafluoroisopropanol at 25° C. The content of prepolymer in the segmented block copolymers may also vary, generally in the range of from about 1 to about 99 weight percent, based on the total weight of the copolymer.

The copolymers of the present invention can be prepared by conventional polymerization techniques well known in the art, for example, as described in U.S. Pat. No. 4,653,497. In the case of the segmented block copolymers, the prepolymer is dissolved in and then reacted with a molten lactone monomer or monomers in the presence of an organometallic catalyst at elevated temperatures. The organometallic catalyst is preferably a tin compound, e.g. stannous 2-ethylhexanoate, and is present in the monomer mixture at a molar ratio of the sum of all of the monomers to catalyst preferably ranging from 5,000:1 to 80,000:1. The initiator is typically an alkanol, a glycol, a hydroxy acid, or an amine, and is present in the monomer mixture at a molar ratio of the sum of all of the monomers to initiator ranging from 400:1 to 2000:1. The copolymerization can be carried out at a temperature range from 100° C. to 220° C., preferably from 160° C. to 200° C., until the desired copolymer is formed; generally no longer than 16 hours is required. Alternatively, the copolymerization can be carried out in two or more stages at different temperatures. For example, the reaction temperature can be maintained at a certain temperature between 100° C. and 140° C. for a short time period between ten minutes and two hours, perhaps to allow the prepolymer to fully dissolve into a mixture of molten comonomers without too many transesterification reactions occurring, and then, the reaction temperature is increased to a higher temperature between 180° C. and 200° C. for a longer period of time, usually between two and forty-eight hours. Additionally, these copolymers may also be prepared using solution or suspension polymerization methods as substantially as described by Jan Nieuwenhuis in *Clinical Materials*, vol. 10, 1992 pages 59–67.

One preferred method for preparing copolymers containing repeating units of 6,6-dialkyl-1,4-dioxepan-2-one is to polymerize the cyclic dimer of 6,6-dialkyl-1,4-dioxepan-2-one, isolate the resulting poly[6,6-dialkyl-1,4-dioxepan-2-one] (PDAD), and then react this polymer with another lactone monomer or with a mixture of lactone monomers in the molten state. This two stage process may be carried out as two discreet reactions or as a two step, one pot procedure. For example, the cyclic dimer of 6,6-dimethyl-1,4-dioxepan-2-one is melt polymerized at 185° C. using stannous 2-ethyl-hexanoate as the Lewis acid catalyst and diethylene glycol as the initiator. The PDAD may be isolated and used as prepared if the conversion is high enough, or purified by first dissolving it into chloroform and then precipitating the polymer into an excess of methanol. The precipitated polymer is collected by suction filtration and vacuum dried at room temperature. In any case, the PDAD is then dissolved in a molten lactone monomer or a molten mixture of lactone monomers usually at a relatively low temperature between 100° C. and 140° C. Lactone monomers such as glycolide, L-lactide, 1,4-dioxan-2-one, ε-caprolactone, or 1,3-dioxan-2-one can be used. After the PDAD has dissolved completely and a homogeneous solution has been obtained, the reaction temperature is raised to a temperature between 175° C. and 200° C. The only exception to this general procedure is when 1,4-dioxan-2-one is employed in which case the temperature is maintained at 110° C. for the duration of the entire reaction. The reaction times are varied depending upon the desired mechanical properties which are determined in part by the microstructure of segmented block copolymer and by the amount of transesterification that is allowed to occur during the second stage of the synthesis.

The copolymers of this invention can be melt processed by numerous methods to prepare a vast array of useful devices. These copolymers can be injection or compression molded to make implantable medical and surgical devices, especially wound closure devices. The preferred wound closure devices are surgical clips, staples, and suture anchors.

Alternatively, the copolymers can be extruded to generate fibers. The filaments so produced may be fabricated into sutures or ligatures, attached to surgical needles, packaged, and sterilized by known techniques. The polymers of the present invention may be spun as multifilament yarn and woven or knitted to form sponges or gauze (nonwoven sheets may also be prepared) or used in conjunction with other molded structures as prosthetic devices within the body of a human or animal where it is desirable that the structure have high tensile strength and desirable levels of compliance and/or ductility. Useful embodiments include tubes, including branched tubes, for artery, vein or intestinal repair, nerve guides, tendon splicing, sheets for tying up and supporting damaged surface abrasions, particularly major abrasions, or areas where the skin and underlying tissues are damaged or surgically removed.

Additionally, the copolymers can be molded to form films which, when sterilized, are useful as adhesion prevention barriers. The copolymers of this invention can also be processed by solvent casting techniques, particularly for those applications where a drug delivery matrix is desired.

In more detail, the surgical and medical uses of the filaments, films, and molded articles of the present invention include, but are not necessarily limited to knitted products, woven or nonwoven, and molded products including:

a. burn dressings
b. hernia patches
c. medicated dressings
d. fascial substitutes
e. gauze, fabric, sheet, felt or sponge for liver hemostasis
f. gauze bandages
g. arterial graft or substitutes
h. bandages for skin surfaces
i. suture knot clips
j. orthopedic pins, clamps, screws, and plates
k. clips (e.g., for vena cava)
l. staples
m. hooks, buttons, and snaps
n. bone substitutes (e.g., mandible prosthesis)
o. intrauterine devices (e.g., spermicidal devices)
p. draining or testing tubes or capillaries
q. surgical instruments
r. vascular implants or supports
s. vertebral discs
t. extracorporeal tubing for kidney and heart/lung machines
u. artificial skin and others
v. catheters.

In preferred embodiments, the copolymers of this invention have a degree of crystallinity and a molecular weight which render the copolymers suitable for extrusion into fibers or films, or for injection molding into surgical devices. Advantageously, the crystallinity of the copolymers will be greater than about 10 percent and most preferably above 25 percent as measured by x-ray diffraction to enable the copolymer to maintain its structural integrity at the elevated temperatures that may be encountered during the shipping and storage of surgical devices. Preferably, the inherent viscosity of the crystalline copolymers will range from about 0.8 to about 4.0, more preferably from about 1.2 to about 2.0 dL/g in a 0.1 g/dL solution of hexafluoroisopropyl alcohol (HFIP) at 25° C. A copolymer with an inherent viscosity below about 0.8 dL/g generally lacks the mechanical properties required for surgical devices, and a copolymer with an inherent viscosity above about 4.0 dL/g is generally too viscous for melt processing.

After the desired copolymer is prepared, filaments exhibiting the requisite properties for use as surgical sutures may be prepared using conventionally accepted methods well known in the art by first melt extruding the copolymer through a spinnerette to prepare fibers, drawing the fibers to create molecular orientation, and then annealing the oriented fibers to enhance their performance characteristics. U.S. Pat. Nos. 4,643,191, 4,653,497, and 5,007,923 describe in detail the testing procedures suitable for determining the mechanical and biological properties of the monofilaments described in the attached examples.

In another embodiment of the present invention, the inventive copolymers may also be used as coatings for sutures and the like to improve the knot strengths and the tiedown properties, as well as to reduce the tissue drag of sutures. Conventional coating procedures can be used to apply the coating to sutures. A preferred method of applying the coating is to continuously pull the suture to be coated through a solution containing in the range of from about 1 to about 20 weight percent copolymer. The suture is pulled through the coating solution in a vertical direction to insure uniform drainage. The freshly coated fiber would then be pulled continuously through a drying tunnel, taken up on a wind-up wheel and vacuum dried overnight at room temperature.

This coating is ideally suited for applying to braided sutures, since braided sutures generally have chartsty or rough tie-down properties. The coating may be applied to monofilament or braided absorbable or nonabsorbable sutures. Suitable absorbable sutures may be made from naturally derived materials including but not limited to catgut and collagen, or from synthetic absorbable materials including but not limited to homopolymers of glycolide, L-lactide, $\epsilon$-caprolactone, and 1,4-dioxan-2-one and copolymers of glycolide, L-lactide, D,L-lactide, $\epsilon$-caprolactone, 1,3-dioxan-2-one, 1,4-dioxan-2-one, 1,5-dioxepan-2-one and 1,4-dioxepan-2-one. Suitable nonabsorbable sutures may be made from naturally occurring, nonabsorbable materials including but not limited to silk, cotton, and linen or synthetic nonabsorbable materials including but not limited to polyesters, polyamides (e.g., nylon, nylon 6, nylon 66 etc.), and polyolefins (e.g., polyethylene and polypropylene).

Sutures coated with the copolymers of this invention are desirable because they have a more slippery feel, thus making it easier for the surgeon to slide a knot down the suture to the site of surgical trauma. In addition, the suture can be passed more easily through body tissue thereby reducing tissue trauma. These advantages are exhibited in comparison to sutures which do not have their surfaces coated with the polymer of this invention. In this particular application (suture coating), it may be advantageous to use copolymers with low molecular weights including copolymers having inherent viscosities in the range of 0.15 dL/g to 0.75 dL/g in a 0.1 g/dL solution of HFIP) at 25° C.

In another embodiment of the present invention, the copolymers of 6,6-dialkyl-1,4-dioxepan-2-one can be used to coat surgical needles in order to facilitate passage through tissue. The amount of coating applied to the surface of the needle is an amount which creates a layer with a thickness ranging preferably between about 2 to about 20 microns, more preferably between about 4 to about 8 microns. If the amount of coating on the needle were such that the thickness of the coating layer was greater than about 20 microns, or if the thickness was less than about 2 microns, then the desired performance of the needle as it is passed through tissue may not be achieved.

In another embodiment of the present invention, the copolymers of 6,6-dialkyl-1,4-dioxepan-2-one can be used as a drug delivery matrix. To form this matrix, the copolymer would be mixed with a therapeutic agent. The variety of different therapeutic agents which can be used in conjunction with the copolymers of the present invention is vast. In general, therapeutic agents which may be administered via the pharmaceutical compositions of the invention include, without limitation: antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered orally, parenterally, subcutaneously, vaginally or anally. Matrix formulations may be formulated by mixing one or more therapeutic agents with the copolymer. The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001% to about 70%, more typically about 0.001% to about 50%, most typically about 0.001% to about 20% by weight of the matrix.

The quantity and type of copolymer incorporated into the drug delivery matrix will vary depending on the release profile desired and the amount of drug employed. The product may contain blends of copolymer to provide the required release profile or consistency to a given formulation.

Upon contact with body fluids, the copolymer undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Individual formulations of drug and copolymer may be tested in appropriate in vitro and in vivo models to achieve the desired drug release profile. For example, a drug could be formulated with a copolymer and orally administered to an animal. The drug release profile could then be monitored by appropriate means such as, by taking blood samples at specific times and assaying the samples for drug concentration. Following this or similar procedures, those skilled in the art will be able to prepare a variety of formulations.

The copolymers of the present invention and homopolymers of 6,6-dialkyl-1,4-dioxepan-2-one may be blended together or may be blended with other absorbable or nonabsorbable polymers in order to achieve new properties not obtained by copolymerization methods. The copolymers (i.e. containing two or more kinds of repeating unit) include statistically random, block, segmented block copolymers and graft copolymers. Suitable lactone monomers may be selected from, but not limited to, the group consisting of glycolide, D-lactide, L-lactide, D,L-lactide, meso-lactide, ε-caprolactone, 1,4-dioxan-2-one, 1,3-dioxan-2-one, 1,4-dioxepan-2-one, 1,5-dioxepan-2-one and combinations thereof. Additionally, 6,6-dialkyl-1,4-dioxepan-2-one can be blended with polyoxaesters such as those described in U.S. Pat. No. 5,464,929 (which is hereby incorporated by reference herein). The blends may contain about 1 weight percent to about 99 weight percent of the aliphatic polyester derived from 6,6-dialkyl-1,4-dioxepan-2-one or its cyclic dimer.

In yet another embodiment of the present invention polymers formed from 6,6-dialkyl-1,4-dioxepan-2-one or its cyclic dimer may be used to form polyoxaesters. The polyoxaester may be formed by copolymerizing the diol (or polydiol) of formula VI and the aliphatic polyoxycarboxylic acid of formula V described in U.S. Pat. No. 5,464,929 in a condensation polymerization with the aliphatic polyester derived from 6,6-dialkyl-1,4-dioxepan-2-one or its cyclic dimer described above to form a polymer generally of the formula:

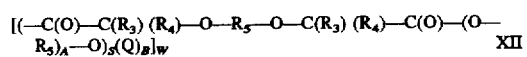

or

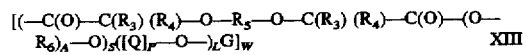

wherein R
3 and R$_4$ are independently selected from the group consisting of hydrogen or an alkyl group containing from 1 to 8 carbon atoms and R$_5$ is an alkylene containing from 2 to 12 carbon atoms or is an oxyalkylene group of the following formula:

$$-[(CH_2)_C-O-]_D-(CH_2)_E- \qquad IV$$

wherein C is an integer in the range of from about 2 to about 5, D is an integer in the range of from about 0 to about 2,000 and preferably will be an integer from 0 to 12; and E is an integer in the range of from about 2 to about 5, except where D is zero in which event E will be an integer from 2 to 12; R$_6$ is an alkylene unit containing from 2 to 8 methylene units; A is an integer in the range of from 1 to about 2,000 and preferably from 1 to about 1000; B is an integer in the range of from 1 to n such that the number average molecular weight of aliphatic polyester derived from 6,6-dialkyl-1,4-dioxepan-2-one or its cyclic dimer is less than about 100,000 and preferably less than 40,000; Q is an aliphatic polyester derived from 6,6-dialkyl-1,4-dioxepan-2-one or its cyclic dimer; P is an integer in the range of from 1 to m such that the number average molecular weight of the formula

is less than about 100,000 and preferably less than 40,000; G represents the residue minus from 1 to L hydrogen atoms from the hydroxyl groups of an alcohol previously containing from 1 to about 200 hydroxyl groups; L is an integer from about 1 to about 200; S is an integer in the range of from about 1 to about 10,000 and preferably from 1 to about 1,000; and W is an integer in the range of from about 1 to about 1,000. Preferably G will be the residue of a dihydroxy alcohol minus both hydroxyl groups. These polymers may be made in the form of random copolymers or block copolymers.

To the diols, aliphatic polyoxycarboxylic acids and 6,6-dialkyl-1,4-dioxepan-2-one or its cyclic dimer described above there may be added a coupling agent selected from the group consisting of trifunctional or tetrafunctional polyols, oxycarboxylic acids, and polybasic carboxylic acids (or acid anhydrides thereof). The addition of the coupling agents causes the branching of long chains, which can impart desirable properties in the molten state to the polyester prepolymer. Examples of suitable polyfunctional coupling agents include trimethylolpropane, glycerin, pentaerythritol, malic acid, citric acid, tartaric acid, trimesic acid, propane tricarboxylic acid, cyclopentane tetracarboxylic anhydride and combinations thereof.

The amount of coupling agent to be added before gelation occurs is a function of the type of coupling agent used and the polymerization conditions of the polyoxaester or molecular weight of the prepolymer to which it is added. Generally in the range of from about 0.1 to about 10 mole percent of a trifunctional or a tetrafunctional coupling agent may be added based on the moles of aliphatic polyoxaester polymers present or anticipated from the synthesis.

The polymers, copolymers, and blends of the present invention can be crosslinked to modify the mechanical properties. Crosslinking can be accomplished by the addition of crosslinking agents or irradiation (such as gamma irradiation). In particular, crosslinking can be used to control the water swellablity of said invention.

The following examples are intended to illustrate the preferred embodiments and are in no way intended to limit the scope of the claimed invention. As used in the examples, PMDP, PDS, PGA and PLA refer to polymers of 6,6-dimethyl-1,4-dioxepan-2-one, 1,4-dioxan-2-one, glycolide and L-lactide, respectively.

EXAMPLE 1

Synthesis of Poly[6-dimethyl-1,4-dioxepan-2-one]

A flame dried, 5 mL ampoule was charged with 1 gram (3.5 mmol) of 3,3,10,10-tetramethyl-1,5,8,12-tetraoxa-cyclotetradecane-7,14-dione (TMD), the cyclic dimer of 6,6-dimethyl-1,4-dioxepan-2-one, and 11 µL (3.7 µmol) of a 0.33M solution of stannous 2-ethyl-hexanoate in toluene. The ampoule was evacuated and flushed with nitrogen gas three times; an inert atmosphere was maintained during the entire polymerization reaction. The reaction mixture was heated to 190° C. in an oil bath while stirring with a magnetic stirrer bar. The temperature was maintained between 190° C. and 195° C. for about 3 hours, and then, reduced to 160°–165°0 C. and held there for about 10 hours. The poly[6,6-dimethyl-1,4-dioxepan-2-one] (PDMD) was isolated and characterized. The inherent viscosity was measured in hexafluoroisopropanol (HFIP) at 25° C. [c=0.1 g/dL] and was found to be 0.87 dL/g. The melting point range of this sample of PDMD was measured on a Fisher Johns apparatus and was found to 58°–63° C. (uncorrected). 300 MHz proton NMR (hexafluoroacetone sesguideuterate (HFAD)/deuterobenzene ($C_6D_6$), ppm) δ 0.9 [singlet, 6H], 3.25 [singlet, 2H], 4.0 [singlet, 2H], 4.1 [singlet, 2H]. The percent conversion was calculated using 300MHz proton NMR spectroscopy by integrating the areas under the methylene singlets located at δ 3.25 for PDMD and at δ 3.17 for TMD and found to be 95 mole percent. After vacuum drying at 80° C. for about 16 hours, the amount of residual TMD was reduced from 5 mole percent to 2.1 mole percent. The glass transition temperature of this sample of PDMD was –6° C., and its melting point was 65° C. as measured by differential scanning calorimetry (DSC) at 20° C./minute under nitrogen. The number average molecular weight was 23,000 g/mole and the weight average molecular weight was 58,000 g/mole as determined by gel permeation chromatography (GPC) using polymethacrylate (PMMA) standards in HFIP.

EXAMPLE 2

Synthesis of Poly[6,6-dimethyl-1,4-dioxepan-2-one]

A flame dried, 5 mL ampoule was charged with 1.44 grams (5 mmol) of TMD and 15 µL (5 µmol) of a 0.33M solution of stannous octoate in toluene. The ampoule was evacuated and flushed with nitrogen gas three times; an inert atmosphere was maintained during the entire polymerization reaction. The reaction mixture was heated to 190° C. in an oil bath while stirring with a magnetic stirrer bar. The temperature was maintained between 190° C. and 195° C. for about 1 hour, and then, reduced to 100° C. and held there for about 5 hours. The PDMD was isolated and vacuum dried for 32 hours. The inherent viscosity was measured in HFIP at 25° C. [c=0.1 g/dL] and was found to be 0.75 dL/g. The melting point range of this PDMD sample was measured on a Fisher Johns apparatus and was found to 85°–92° C. (uncorrected). The percent conversion was calculated using 300 MHz proton NMR spectroscopy and found to be 73 mole percent.

EXAMPLE 3

Purification of Poly[6,6-dimethyl-1,4-dioxepan-2-one]

The polymer of Example 2 was extracted with ethyl ether using a Soxhelet extractor for about two days to remove unreacted monomer. The extraction residue was vacuum dried at 50° C. for 16 hours. Sixty-nine percent of the polymer was recovered. The amount of residual TMD was reduced to 1.4 mole percent, while the inherent viscosity increased to 1.1 dL/g as measured in HFIP at 25° C. [c=0.10 g/dL]. The glass transition temperature of this sample of PDMD was –6° C., and its melting point was 64° C. as measured by DSC at 20° C./minute under nitrogen. The number average molecular weight was 22,000 g/mole and the weight average molecular weight was 64,000 g/mole as determined by GPC using PMMA standards in HFIP.

EXAMPLE 4

Synthesis of Poly[6,6-dimethyl-1,4-dioxepan-2-one]

A flame dried, 5 mL ampoule was charged with 1 gram (3.5 mmol) of TMD and 11 µL (3.7 µmol) of a 0.33M solution of stannous 2-ethyl-hexanoate in toluene. The ampoule was evacuated and flushed with nitrogen gas three times; an inert atmosphere was maintained during the entire polymerization reaction. The reaction mixture was heated to 190° C. in an oil bath while stirring with a magnetic stirrer bar. The temperature was maintained between 190° C. and 195° C. for about one hour, and then, reduced to 160°–165° C. and held there for about 23 hours. The inherent viscosity of this crude PDMD was measured in HFIP at 25° C. [c=0.1 g/dL] and was found to be 0.91 dL/g. The polymer was then extracted with ethyl ether using a Soxhelet extractor for 24 hours to remove unreacted monomer. The extraction residue was vacuum dried at 50° C. for about 16 hours. Ninety-six percent of the polymer was recovered. The inherent viscosity of the extracted polymer was unchanged from the original polymer, and the amount of residual TMD was 0.3 mole percent as determined by 300 MHz proton NMR spectroscopy. The glass transition temperature of this sample of PDMD was −8° C., and its melting point was 77° C. as measured by DSC at 20° C./minute under nitrogen. The number average molecular weight was 29,000 g/mole and the weight average molecular weight was 74,000 g/mole as determined by GPC using PMMA standards in HFIP.

EXAMPLE 5

In Vitro Hydrolysis

The in vitro absorption rates of the polymers from examples 1 and 2 were determined as follows: for each sample, 100 mg were placed in a jar containing 100 mL of phosphate buffered saline (0.2M in phosphate, pH 7.27), closed tightly, and immersed in a water bath set at 50° C. After three months of incubation, about 30 weight percent of the PDMD samples had been absorbed.

In addition, a hydrolysis study was carried out on the polymer from example 3 using 300 MHz proton NMR spectroscopy to monitor the progress of the reaction. The polymer was suspended in unbuffered D$_2$O at 95° C. After 115 hours, the PDMD was completely hydrolyzed into the corresponding hydroxyacid. At intermediate time periods, significant concentrations of water soluble oligomers were observed.

We claim:

1. A copolymer comprising a first repeating unit of the chemical formula:

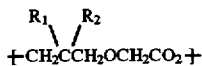

in which R$_1$ and R$_2$ are independently alkyl groups selected from the group consisting of methyl, ethyl and propyl groups and a second repeating unit is generated from a monomer selected from the group of glycolic acid, lactic acid, glycolide, lactide (l, d, dl and meso), 3-methyl-1,4-dioxan-2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1,3-dioxan-2-one, epsilon-caprolactone and combinations thereof and the first repeating unit is less than 45 weight percent of the total weight of the copolymer.

2. The copolymer of claim 1 wherein R$_1$ and R$_2$ are the same alkyl group.

3. The copolymer of claim 2 wherein the second repeating unit has a chemical formula selected from the group consisting of:

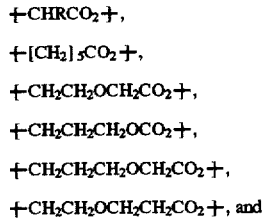

combinations of two or more thereof wherein R is a hydrogen atom or methyl group.

4. The copolymer of claim 3 wherein the copolymer is selected from the group consisting of:

a) a copolymer comprising the reaction product of a prepolymer of the first repeating unit the remainder of the copolymer being the second repeating unit;

b) a random copolymer comprising the first repeating unit and the second repeating unit;

c) a copolymer comprising the reaction product of a prepolymer containing the second repeating unit and the remainder of the copolymer being the first repeating unit; and d) a copolymer comprising the reaction product of a prepolymer containing less than 45 weight percent of the first repeating unit and greater than 55 weight percent of the second repeating unit in the prepolymer and the remainder of the copolymer being the second repeating unit.

5. The copolymer of claim 1 wherein the copolymer is the reaction product of a prepolymer of the first repeating unit and the remainder of the copolymer is the second repeating unit.

6. The copolymer of claim 1 wherein the copolymer is the statistically random copolymer of the first repeating unit and the second repeating unit.

7. The copolymer of claim 1 wherein the copolymer comprises the reaction product of a prepolymer containing the second repeating unit and the remainder of the copolymer being the first repeating unit.

8. The copolymer of claim 1 wherein the copolymer is the reaction product of a prepolymer containing less than 45 weight percent of the first repeating unit and greater than 55 weight percent of the second repeating unit in the prepolymer and the remainder of the copolymer being the second repeating unit.

9. The copolymer of claim 3 wherein the second repeating unit is of the chemical formula:

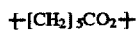

10. The copolymer of claim 7 wherein additionally present with the first repeating unit in the remainder of the copolymer is the second repeating unit.

11. A surgical device comprising a copolymer composed of a first repeating unit of the chemical formula:

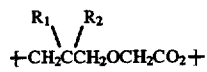

in which R$_1$ and R$_2$ are independently alkyl groups selected from the group consisting of methyl, ethyl and propyl groups and a second repeating unit is generated from a monomer selected from the group of glycolic acid, lactic acid, glycolide, lactide (l, d, dl and meso), 3-methyl-1,4-dioxan-2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1,3-dioxan-2-one, epsilon-caprolactone and combinations thereof and the first repeating unit is less than 45 weight percent of the total weight of the copolymer.

12. The surgical device of claim 11 wherein R$_1$ and R$_2$ are the same alkyl group.

13. The surgical device of claim 12 wherein the second repeating unit has a chemical formula selected from the group consisting of:

$+CHRCO_2+$, $+[CH_2]_5CO_2+$, $+CH_2CH_2OCH_2CO_2+$, $+CH_2CH_2CH_2OCO_2+$, $+CH_2CH_2CH_2OCH_2CO_2+$, $+CH_2CH_2OCH_2CH_2CO_2+$ and combinations of two or more thereof wherein R is a hydrogen atom or a methyl group.

14. The surgical device of claim 13 wherein the copolymer is selected from the group consisting of:
   a) a copolymer comprising the reaction product of a prepolymer of the first repeating unit the remainder of the copolymer being the second repeating unit;
   b) a random copolymer comprising the first repeating unit and the second repeating unit;
   c) a copolymer comprising the reaction product of a prepolymer containing the second repeating unit and the remainder of the copolymer being the first repeating unit; and
   d) a copolymer comprising the reaction product of a prepolymer containing less than 45 weight percent of the first repeating unit and greater than 55 weight percent of the second repeating unit in the prepolymer and the remainder of the copolymer being the second repeating unit.

15. The surgical device of claim 11 wherein the surgical device is selected from the group consisting of sutures, ligaments, ribbons, pins, screws, clamps, plates, films, medical dressings, hernia patches, gauze, meshes, fabrics, felts, sponges, surgical staples, hemostatic clips, suture knot clips, hooks, buttons, snaps, bone substitutes and vascular implants.

16. The surgical device of claim 11 wherein the copolymer is the reaction product of a prepolymer of the first repeating unit and the remainder of the copolymer is the second repeating unit.

17. The surgical device of claim 11 wherein the copolymer is a statistically random copolymer comprising the first repeating unit and the second repeating unit.

18. The surgical device of claim 11 wherein the copolymer is the reaction product of a prepolymer containing the second repeating unit the remainder of the copolymer being the first repeating unit.

19. The surgical device of claim 11 wherein the copolymer is a copolymer comprising the reaction product of a prepolymer containing less than 45 weight percent of the first repeating unit and greater than 55 weight percent of the second repeating unit in the prepolymer and the remainder of the copolymer being the second repeating unit.

20. The surgical device of claim 11 wherein the surgical device is a suture.

21. The surgical device of claim 13 wherein the surgical device is a suture.

22. The surgical device of claim 21 wherein the suture is attached to at least one needle.

23. The surgical device of claim 11 wherein additionally present with the first repeating unit in the remainder of the copolymer is the second repeating unit.

24. A suture coated with a copolymer composed of a first repeating unit of the chemical formula:

$$+CH_2\underset{\underset{\displaystyle R_2}{|}}{\overset{\overset{\displaystyle R_1}{|}}{C}}CH_2OCH_2CO_2+$$

in which $R_1$ and $R_2$ are independently alkyl groups selected from the group consisting of methyl, ethyl and propyl groups and a second repeating unit is generated from a monomer selected from the group of glycolic acid, lactic acid, glycolide, lactide (1, d, dl and meso), 3-methyl-1,4-dioxan-2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1,3-dioxan-2-one, epsilon-caprolactone and combinations thereof and the first repeating unit is less than 45 weight percent of the total weight of the copolymer.

25. The suture coated with the copolymer of claim 24 wherein $R_1$ and $R_2$ are the same alkyl group.

26. The suture coated with the copolymer of claim 25 wherein the second repeating unit has a chemical formula selected from the group consisting of:

$+CHRCO_2+$, $+[CH_2]_5CO_2+$, $+CH_2CH_2OCH_2CO_2+$, $+CH_2CH_2CH_2OCO_2+$, $+CH_2CH_2CH_2OCH_2CO_2+$, $+CH_2CH_2OCH_2CH_2CO_2+$ and combinations of two or more thereof wherein R is a hydrogen atom or a methyl group.

27. The suture coated with the copolymer of claim 26 wherein the copolymer is selected from the group consisting of:
   a) a copolymer comprising the reaction product of a prepolymer of the first repeating unit the remainder of the copolymer being the second repeating unit;
   b) a random copolymer comprising the first repeating unit and the second repeating unit;
   c) a copolymer comprising the reaction product of a prepolymer containing the second repeating unit and the remainder of the copolymer being the first repeating unit; and
   d) a copolymer comprising the reaction product of a prepolymer containing less than 45 weight percent of the first repeating unit and greater than 55 weight percent of the second repeating unit in the prepolymer and the remainder of the copolymer being the second repeating unit.

28. The coated suture of claim 24 wherein the copolymer is the reaction product of a prepolymer of the first repeating unit and the remainder of the copolymer is the second repeating unit.

29. The coated suture of claim 24 wherein the copolymer is a statistically random copolymer comprising the first repeating unit and the second repeating unit.

30. The coated suture of claim 24 wherein the copolymer is the reaction product of a prepolymer containing the second repeating unit and the remainder of the copolymer being the first repeating unit.

31. The coated suture of claim 24 wherein the copolymer is a copolymer comprising the reaction product of a prepolymer containing less than 45 weight percent of the first repeating unit and greater than 55 weight percent of the second repeating unit in the prepolymer and the remainder of the copolymer being the second repeating unit.

32. The copolymer of claim 26 wherein the second repeating unit is of the formula:

$+[CH_2]_5CO_2+$.

33. The coated suture of claim 24 wherein the suture is attached to at least one needle.

34. A surgical device having at least a part thereof made from a polymeric blend composed of at least one first polymer selected from the group consisting of homopolymers and copolymers (including segmented block copolymers and graft copolymers) prepared from monomers selected from the group consisting of glycolic acid, lactic acid, glycolide, L-lactide, D-lactide, D,L-lactide, meso-lactide, 1,4-dioxan-2-one, 1,3-dioxan-2-one, 4,4-dimethyl-1,3-dioxan-2-one, ε-caprolactone, 1,4-dioxepan-2-one, 1,5-dioxepan-2-one and combinations thereof; and a second polymer having a first repeating unit of the chemical formula:

$$+CH_2\underset{\underset{R_1\ \ R_2}{\diagup\diagdown}}{C}CH_2OCH_2CO_2+$$

in which $R_1$ and $R_2$ are independently alkyl groups selected from the group consisting of methyl, ethyl and propyl groups and optionally a second repeating unit is generated from a monomer selected from the group of glycolic acid, lactic acid, glycolide, lactide (1, d, dl and meso), 3-methyl-1,4-dioxan-2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1,3-dioxan-2-one, epsilon-caprolactone and combinations thereof and the first repeating unit is less than 45 weight percent of the total weight of the copolymer.

35. The surgical device of claim 34 wherein $R_1$ and $R_2$ are the same alkyl group.

36. The surgical device of claim 35 wherein the second repeating unit has a chemical formula selected from the group consisting of:

$+CHRCO_2+$, $+[CH_2]_5CO_2+$, $+CH_2CH_2OCH_2CO_2+$, $+CH_2CH_2CH_2OCO_2+$, $+CH_2CH_2CH_2OCH_2CO_2+$, $+CH_2CH_2OCH_2CH_2CO_2+$ and combinations of two or more thereof wherein R is a hydrogen atom or a methyl group.

37. The surgical device of claim 34 wherein the copolymer is selected from the group consisting of:
  a) a copolymer comprising the reaction product of a prepolymer of the first repeating unit the remainder of the copolymer being the second repeating unit;
  b) a statistically random copolymer comprising the first repeating unit and the second repeating unit;
  c) a copolymer comprising the reaction product of a prepolymer containing the second repeating unit and the remainder of the copolymer being the first repeating unit; and
  d) a copolymer comprising the reaction product of a prepolymer containing less than 45 weight percent of the first repeating unit and greater than 55 weight percent of the second repeating unit in the prepolymer and the remainder of the copolymer being the second repeating unit.

38. The surgical device of claim 34 wherein the surgical device is selected from the group consisting of sutures, ligaments, ribbons, pins, screws, clamps, plates, films, medical dressings, hernia patches, gauze, meshes, fabrics, felts, sponges, surgical staples, hemostatic clips, suture knot clips, hooks, buttons, snaps, bone substitutes and vascular implants.

39. The surgical device of claim 34 wherein the second polymer is the reaction product of a prepolymer of the first repeating unit and the remainder of the copolymer is the second repeating unit.

40. The surgical device of claim 34 wherein the second polymer is a statistically random copolymer comprising the first repeating unit and the second repeating unit.

41. The surgical device of claim 34 wherein the second polymer is the reaction product of a prepolymer containing the second repeating unit the remainder of the copolymer being the first repeating unit.

42. The surgical device of claim 34 wherein the copolymer is a copolymer comprising the reaction product of a prepolymer containing less than 45 weight percent of the first repeating unit and greater than 55 weight percent of the second repeating unit in the prepolymer and the remainder of the copolymer being the second repeating unit.

43. The surgical device of claim 36 wherein the surgical device is selected from the group consisting of sutures, ligaments, ribbons, pins, screws, clamps, plates, films, medical dressings, hernia patches, gauze, meshes, fabrics, felts, sponges, surgical staples, hemostatic clips, suture knot clips, hooks, buttons, snaps, bone substitutes and vascular implants.

44. The surgical device of claim 43 wherein the surgical device is a surgical staple.

45. The surgical device of claim 44 wherein the surgical device is a hemostatic clip.

46. The surgical device of claim 34 wherein additionally present with the first repeating unit in the remainder of the copolymer is the second repeating unit.

47. A polymeric blend composed of at least one first polymer selected from homopolymers and copolymers (including segmented block copolymers and graft copolymers) prepared from monomers selected from the group consisting of glycolic acid, lactic acid, glycolide, L-lactide, D-lactide, D,L-lactide, meso-lactide, 1,4-dioxan-2-one, 1,3-dioxan-2-one, 4,4-dimethyl-1,3-dioxan-2-one, ε-caprolactone, 1,4-dioxepan-2-one, 1,5-dioxepan-2-one and combinations thereof; and a second polymer having a first repeating unit of the chemical formula:

$$+CH_2\underset{\underset{R_1\ \ R_2}{\diagup\diagdown}}{C}CH_2OCH_2CO_2+$$

in which $R_1$ and $R_2$ are independently alkyl groups selected from the group consisting of methyl, ethyl and propyl groups and a second repeating unit is generated from a monomer selected from the group of glycolic acid, lactic acid, glycolide, lactide (1, d, dl and meso), 3-methyl-1,4-dioxan-2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4- dimethyl-1,3-dioxan-2-one, epsilon-caprolactone and combinations thereof and the first repeating unit is less than 45 weight percent of the total weight of the copolymer.

48. The polymeric blend of claim 47 wherein $R_1$ and $R_2$ are the same alkyl group.

49. The polymeric blend of claim 48 wherein the second repeating unit has a chemical formula selected from the group consisting of:

$+CHRCO_2+$, $+[CH_2]_SCO_2+$, $+CH_2CH_2OCH_2CO_2+$, $+CH_2CH_2CH_2OCO_2+$, $+CH_2CH_2CH_2OCH_2CO_2+$, $+CH_2CH_2OCH_2CH_2CO_2+$ and combinations of two or more thereof wherein R is a hydrogen atom or a methyl group.

50. The polymeric blend of claim 47 wherein the copolymer is selected from the group consisting of:
   a) a copolymer comprising the reaction product of a prepolymer of the first repeating unit the remainder of the copolymer being the second repeating unit;
   b) a statistically random copolymer comprising the first repeating unit and the second repeating unit;
   c) a copolymer comprising the reaction product of a prepolymer containing the second repeating unit and the remainder of the copolymer being the first repeating unit; and
   d) a copolymer comprising the reaction product of a prepolymer containing less than 45 weight percent of the first repeating unit and greater than 55 weight percent of the second repeating unit in the prepolymer and the remainder of the copolymer being the second repeating unit.

51. A polyoxaester having a formula selected from the group consisting of $[(-C(O)-C(R_3)-(R_4)-O-R_5-O-C(R_3)-(R_4)-C(O)-(O-R_6)_A-O)_S(Q)_B]_W$     XII and $[(-C(O)-C(R_3)-(R_4)-O-R_5-O-C(R_3)-(R_4)-C(O)-(O-R_6)_A-O)_S([Q]_P-O-)_LG]_W$     XIII wherein $R_3$ and $R_4$ are independently selected from the group consisting of hydrogen or an alkyl group containing from 1 to 8 carbon atoms and $R_5$ is an alkylene containing from 2 to 12 carbon atoms or is an oxyalkylene group of the following formula:

$-[(CH_2)_C-O-]_D-(CH_2)_E$     IV wherein C is an integer in the range of from about 2 to about 5, D is an integer in the range of from about 0 to about 2,000, and E is an integer in the range of from about 2 to about 5 except when D is zero in which event E is an integer from 1 to 12; $R_6$ is an alkylene unit containing from 2 to 8 methylene units; A is an integer in the range of from 1 to about 2,000; B is an integer in the range of from 1 to n such that the number average molecular weight of Q is less than about 100,000; Q is an aliphatic polyester having at least a first repeating unit of the chemical formula:

$+CH_2C(R_1)(R_2)CH_2OCH_2CO_2+$ wherein $R_1$ and $R_2$ are independently alkyl groups selected from the group consisting of methyl, ethyl and propyl groups; P is an integer in the range of from 1 to m such that the number average molecular weight of the formula:

$([Q]_P-O-)_LG$ is less than about 100,000; G represents the residue minus from 1 to L hydrogen atoms from the hydroxyl groups of an alcohol previously containing from 1 to about 200 hydroxyl groups; L is an integer from about 1 to about 200; and S is an integer in the range of from about 1 to about 1,000; and W is an integer in the range of from about 1 to about 1,000.

52. The polyoxaester of claim 51 wherein the aliphatic polyester additionally contains a second repeating unit generated from a monomer selected from the group of glycolic acid, lactic acid, glycolide, lactide (1, d, dl and meso), 3-methyl-1,4-dioxan-2,5-dione, 3,3-diethyl-1,4-dioxan-2,5-one, 1,4-dioxan-2-one, 1,4-dioxepan-2-one, 1,5-dioxepan-2-one, delta-valerolactone, epsilon-decalactone, pivalolactone, gamma-butyrolactone, ethylene carbonate, 1,3-dioxan-2-one, 4,4-dimethyl-1,3-dioxan-2-one, epsilon-caprolactone and combinations thereof.

53. The polyoxaester of claim 52 wherein the first repeating unit is less than 45 weight percent of the total weight of the copolymer.

54. The polyoxaester of claim 51 wherein $R_1$ and $R_2$ are the same alkyl group.

55. The polyoxaester of claim 54 wherein the second repeating unit has a chemical formula selected from the group consisting of:

$+CHRCO_2+$, $+[CH_2]_SCO_2+$, $+CH_2CH_2OCH_2CO_2+$, $+CH_2CH_2CH_2OCO_2+$, $+CH_2CH_2CH_2OCH_2CO_2+$, $+CH_2CH_2OCH_2CH_2CO_2+$ and combinations of two or more thereof wherein R is a hydrogen atom or a methyl group.

56. The polyoxaester of claim 47 wherein the aliphatic polyester is a copolymer selected from the group consisting of:
   a) a copolymer comprising the reaction product of a prepolymer of the first repeating unit the remainder of the copolymer being the second repeating unit;
   b) a statistically random copolymer comprising the first repeating unit and the second repeating unit;
   c) a copolymer comprising the reaction product of a prepolymer containing the second repeating unit and the remainder of the copolymer being the first repeating unit; and
   d) a copolymer comprising the reaction product of a prepolymer containing less than 45 weight percent of the first repeating unit and greater than 55 weight percent of the second repeating unit in the prepolymer and the remainder of the copolymer being the second repeating unit.

57. The copolymer of claim 1 wherein $R_1$ and $R_2$ are methyl groups.

58. The surgical device of claim 11 wherein $R_1$ and $R_2$ are methyl groups.

59. The suture coated with a copolymer of claim 24 wherein $R_1$ and $R_2$ are methyl groups.

60. The surgical device of claim 34 wherein $R_1$ and $R_2$ are methyl groups.

61. The polymeric blend of claim 47 wherein $R_1$ and $R_2$ are methyl groups.

62. The polyoxaester of claim 51 wherein $R_1$ and $R_2$ are methyl groups.

* * * * *